(12) United States Patent
Ensor et al.

(10) Patent No.: US 6,635,462 B1
(45) Date of Patent: Oct. 21, 2003

(54) MUTATED FORM OF ARGININE DEIMINASE

(75) Inventors: Charles Mark Ensor, Lexington, KY (US); Frederick Wayne Holtsberg, Nicholasville, KY (US); Mike A. Clark, Big Pine, FL (US)

(73) Assignee: Phoenix Pharmacologies, Inc., Lexington, KY (US)

( * ) Notice: Subject to any disclaimer, the term of this patent is extended or adjusted under 35 U.S.C. 154(b) by 0 days.

(21) Appl. No.: 09/564,559

(22) Filed: May 4, 2000

Related U.S. Application Data

(63) Continuation-in-part of application No. 09/023,809, filed on Feb. 13, 1998, now Pat. No. 6,183,738.
(60) Provisional application No. 60/046,200, filed on May 12, 1997.

(51) Int. Cl.$^7$ .............. C12N 9/14; C12Q 1/34; C07K 17/00; A61K 38/46; C12P 21/00

(52) U.S. Cl. ............ 435/195; 435/18; 435/69.1; 435/180; 435/181; 435/188; 435/191; 530/350; 424/94.6; 536/23.2

(58) Field of Search .................. 435/18, 69.1, 180, 435/181, 188, 191, 195; 424/94.6; 536/23.2; 530/350

(56) References Cited

U.S. PATENT DOCUMENTS

| | | |
|---|---|---|
| 4,800,159 A | 1/1989 | Mullis et al. ............ 435/172.3 |
| 5,372,942 A | 12/1994 | McGarrity et al. ......... 435/227 |
| 5,474,928 A | 12/1995 | Takaku et al. ............. 435/228 |
| 5,804,183 A | 9/1998 | Filpula et al. ............. 424/94.6 |
| 5,916,793 A | 6/1999 | Filpula et al. ............. 435/195 |
| 6,132,713 A | 10/2000 | Fiipula et al. ............. 424/94.3 |

FOREIGN PATENT DOCUMENTS

| | | |
|---|---|---|
| EP | 0 414 007 A2 | 2/1991 |
| EP | 0 897 011 A2 | 2/1999 |
| JP | 3209338 B2 | 9/2001 |
| WO | 98/33519 | 8/1998 |
| WO | 98/51784 | 11/1998 |

OTHER PUBLICATIONS

Seffernick et al. , J. Bacteriol. 183(8):2405–2410, 2001.*
Broun et al. (Science 282:1315–1317, 1998).*
Van de Loo et al. , Proc. Natl. Acad. Sci. 92:6743–6747, 1995.*
Sugimura et al., "High Sensitivity of Human Melanoma Cell Lines To The Growth Inhibitory Activity Of Mycoplasmal Arginine Deiminase In Vitro", *Melanoma Res.*, 1992, 2, 191–196.
Takaku et al., "In Vivo Anti–Tumor Activity Of Arginine Deiminase Purified From Mycoplasma Arginini", *Int. J. Cancer*, 1992, 51, 244–249.
Miyazaki et al, "Potent Growth Inhibition Of Human Tumor Cells In Culture By Arginine Deiminase Purified From A Culture Medium Of A Mycoplasma–infected Cell Line", *Cancer Res.*, 1990, 50, 4522–4527.
J.B. Jones, "The Effect of Arginine Deiminase on Murine Leukemic Lymphoblasts," *Ph.D. Dissertation, The University of Oklahoma*, 1981, 1–169.
van Wagtendonk et al., "Nitrogen Metabolism in Protozoa", *Comparative Biochemistry of Nitrogen Metabolism* (J.W. Campbell ed.), 1970, 1–56.
Chang et al., "Arginase Modulates Nitric Oxide Production In Activated Macrophages", *Am. J. Physiol: Heart and Circul. Physiol.*, 1998, 274, H342–H348.
McDonald et al., A Caveolar Complex Between The Cationic Amino Acid Transporter 1 And Endothelial Nitric–oxide Synthase May Explain the "Arginine Paradox", *J. Biol. Chem.*, 1997, 272, 31213–31216.
Misawa et al., "High Level Expression Of *Mycoplasma* aginine Deiminase In *Escherichia Coli* And Its Efficient Renaturation As An Anti–Tumor Enzyme", *J. Of Biotechnol.*, 1994, 36, 145–155.
Takaku et al., "Chemical Modification By Polyethylene Glycol Of The Anti–Tumor Enzyme Arginine Deiminase From *Mycoplasma argini*", *Int. J. Cancer Res.*, 1993, 84, 1195–1200.
Abuchowski et al., "Cancer Therapy With Chemically Modified Enzymes. I. Antitumor Properties Of Polyethylene Glycol–Asparaginase Conjugates", *Cancer Biochem. Biophys.*, 1984, 7, 175–186.
Abuchowski et al., "Effect Of Covalent Attachment Of Polyethylene Glycol On Immunogenicity And Circulating Life Of Bovine Liver Catalse", *J. Biol. Chem.*, 1977, 252, 3582–3586.
Parker, et al., "The Effect Of Tumor Size On Concomitant Tumor Immunity", *Cancer Res.*, 1973, 33(1), 33–39.
Zaplipsky and Lee, "Use Of Functionalized Poly(Ethylene Glycol)s for Modification of Polypeptides", *Poly(Ethylene Glycol) Chemistry: Biotechnical and Biomedical Applications* (J.M. Harris, ed., Plenum Press, NY), 1992, Chapter 21, 347–370.
Fenske, J.D., Kenny, G.E., "Role Of Arginine Deiminase In Growth Of *Mycoplasma hominus*", *J. Bacteriol.*, 1976, 126, 501–510.

(List continued on next page.)

*Primary Examiner*—Rebecca E. Prouty
(74) *Attorney, Agent, or Firm*—Woodcock Washburn LLP

(57) ABSTRACT

The present invention discloses arginine deiminase that is genetically modified for more efficient manufacturing and processing. The present invention discloses recombinant DNA molecules and vectors and other therapeutic and pharmaceutical compositions. The present invention also discloses methods for preparing modified arginine deiminase as well as methods of treating cancer and other disease states using modified arginine deiminase.

13 Claims, 2 Drawing Sheets

OTHER PUBLICATIONS

Lang, K, et al., "Catalysis Of Protein Folding By Prolyl Isomerase", *Nature*, 1987, 329, 268–270.

Craig, S., et al., "Single Amino Acid Mutations Block A Late Step In The Folding of β–Lactamase From *Staphylococcus aureus*", *J. Mol. Biol.*, 1985, 185, 681–687.

Joppich, et al., "Peptides Flanked By Two Polymer Chains, 1—Synthesis of Glycl–L–tryptophylglycine Substituted By Poly(ethylene oxide) At Both The Carboxy And The Amino End Groups", *Macromol. Chem.*, 1979, 180, 1381–1385.

Abstract J04121187: Japanese Application No. 1992–188063, Derwent Publications Ltd., London, GB, Apr. 22, 1992.

Harasawa, R. et al., "Nucleotide Sequence of the Arginine Deiminase Gene of *Mycoplasma hominis,*" *Microbiol. Immunol.*, 1992, 36(6), 661–665.

Takaku, H. et al., "Anti–tumor Activity of Arginine Deiminase from *Mycoplasma arginini* and Its Growth–inhibitory Mechanism," *Jpn. J. Cancer Res.*, Sep. 1995, 86(9), 840–846.

International Search Report dated Jan. 11, 2002, issued in corresponding International Application No. PCT/US01/14116.

Fraser, C. et al., "*Borrelia burgdorferi* (section 69 of 70) of the complete genome", Dec. 16, 1997, Database Accession No. AE001183, XP 002211866.

Knodler, Leigh A. et al., "Cloning and Expression of a Prokaryotic Enzyme, Arginine Deiminase., from a Primitive Eukaryote *Giardia intestinalis*", *Journal of Biological Chemistry*, Feb. 20, 1998, 273(8), 4470–4477, XP–002211868.

* cited by examiner

FIG 1. Amino acid sequence of arginine deiminase (ADI) from wild-type *Mycoplasma hominus*

M. hominis ADI    MSVFDSKFNGIHVYSEIGELETVLVHEPGREIDYITPARLDELLFSAILESHDARKEHQS              60
M. hominis ADI    FVKIMKDRGINVVELTDLVAETYDLASKAAKEEFIETFLEETVPVLTEANKKAVRAFLLS             120
M. hominis ADI    KPTHEMVEFMMSGITKYELGVESENELIVDPMPNLYFTRDPFASVGNGVTIHFMRYIVRR            180
M. hominis ADI    RETLFARFVFRNHPKLVKTPWYYDPAMKMPIEGGDVFIYNNETLVVGVSERTDLDTITLL            240
M. hominis ADI    AKNIKANKEVEFKRIVAINVPKWTNLMHLDTWLTMLDKNKFLYSPIANDVFKFWDYDLVN            300
M. hominis ADI    GGAEPQPQLNGLPLDKLLASIINKEPVLIPIGGAGATEMEIARETNFDGTNYLAIKPGLV            360
M. hominis ADI    IGYDRNEKTNAALKAAGITVLPFHGNQLSLGMGNARCMSMPLSRKDVKW                        409

FIG 2. Amino acid sequence of modified arginine deiminase (ADI E112, S210) from *Mycoplasma hominus*

| | | |
|---|---|---|
| ADI E112, S210 | MSVFDSKFNGIHVYSEIGELETVLVHEPGREIDYITPARLDELLFSAILESHDARKEHQS | 60 |
| ADI E112, S210 | FVKIMKDRGINVVELTDLVAETYDLASKAAKEEFIETFLEETVPVLTEANKEAVRAFLLS | 120 |
| ADI E112, S210 | KPTHEMVEFMMSGITKYELGVESENELIVDPMPNLYFTRDPFASVGNGVTIHFMRYIVRR | 180 |
| ADI E112, S210 | RETLFARFVFRNHPKLVKTPWYYDPAMKMSIEGGDVFIYNNETLVVGVSERTDLDTITLL | 240 |
| ADI E112, S210 | AKNIKANKEVEFKRIVAINVPKWTNLMHLDTWLTMLDKNKFLYSPIANDVFKFWDYDLVN | 300 |
| ADI E112, S210 | GGAEPQPQLNGLPLDKLLASIINKEPVLIPIGGAGATEMEIARETNFDGTNYLAIKPGLV | 360 |
| ADI E112, S210 | IGYDRNEKTNAALKAAGITVLPFHGNQLSLGMGNARCMSMPLSRKDVKW | 409 |

MUTATED FORM OF ARGININE DEIMINASE

This application is a continuation-in-part of U.S. patent application Ser. No. 09/023,809, filed Feb. 13, 1998, now U.S. Pat. No. 6,183,738, which claims the benefit of U.S. Provisional Application Serial No. 60/046,200, filed May 12, 1997, each of which is incorporated herein by reference.

FIELD OF THE INVENTION

The present invention is directed to mutations of arginine deiminase for more efficient production and processing and thus improved treatment of cancer and other disease states.

BACKGROUND OF THE INVENTION

It is presently believed that the amino acid arginine may play an important role in mediating certain disease states. For example, it has been reported that tumors such as melanomas, hepatomas, sarcomas and leukemia require arginine for growth. Sugimura et al., *Melanoma Res.* 2:191–196(1992); Takaku et al., Int. *J. Cancer* 51:244–249 (1992); Miyazaki et al, Cancer Res. 50:4522–4527 (1990); J. B. Jones, "The Effect of Arginine Deiminase on Murine Leukemic Lymphoblasts," Ph.D. Dissertation, The University of Oklahoma, pages 1–165 (1981). Malignant melanoma (stage 3) and hepatoma are fatal diseases which kill most patients within one year of diagnosis. In the United States, approximately 16,000 people die from these diseases annually. The incidence of melanoma is rapidly increasing in the United States and is even higher in other countries, such as Australia. The incidence of hepatoma, in parts of the world where hepatitis is endemic, is even greater. For example, hepatoma is one of the leading forms of cancer in Japan and Taiwan.

It has also been reported that many protozoa require arginine for growth and thus arginine may play an important role in many parasitic diseases. van Wagtendonk et al., "Nitrogen Metabolism in Protozoa", in Comparative Biochemistry of Nitrogen Metabolism, pages 1–56 (J. W. Campbell ed. 1970). Arginine (derived from the circulation) has also been shown to be a source of nitrous oxide which can play an important role in mediating septic shock. Chang et al., *Am J. Physiol.* 274:H342–H348 (1998); McDonald et al., *J. BioL Chem.* 272:31213–31216 (1997). Effective treatments for these diseases are urgently needed.

It has been reported that enzymes which degrade nonessential amino acids, such as arginine, may be an effective means of controlling some forms of cancer. For example, arginine deiminase isolated from Pseudomonas putide was described by J. B. Jones, "The Effect of Arginine Deiminase on Murine Leukemic Lymphoblasts," Ph.D. Dissertation, The University of Oklahoma, pages 1–165 (1981). Because arginine deiminase catalyzes the conversion of arginine into citrulline, thus helping to eliminate arginine from the circulation of animals, it is believed that arginine deiminase can be used as an effective therapy for cancer and other disease states where arginine plays a role. Although arginine deiminase is not produced in mammals, it is found in a variety of bacteria, fungi and mycoplasma. Arginine deiminase can be thus be isolated from those organisms which produce it or, in the alternative, the enzyme may be produced using recombinant DNA technology. Misawa et al., *J. Biotechnol.* 36:145–155 (1994).

Certain disadvantages have come to be associated with the isolation of arginine deiminase from organisms. Although effective in killing tumor cells in vitro, arginine deiminase isolated from Pseudomonas pudita failed to exhibit efficacy in vivo because it had little enzyme activity at a neutral pH and was rapidly cleared from the circulation of experimental animals. Arginine deiminase derived from *Mycoplasma arginini* (SEQ ID NO:5) is described, for example, by Takaku et al, Int. *J. Cancer*, 51:244–249 (1992), and U.S. Pat. No. 5,474,928, the disclosures of which are hereby incorporated by reference herein in their entirety. A problem associated with the therapeutic use of such a heterologous protein is its antigenicity. The chemical modification of arginine deiminase from *Mycoplasma arginini*, via a cyanuric chloride linking group, with polyethylene glycol was described by Takaku et al., Int. *J. Cancer Res.* 84:1195–1200 (1993). The modified protein was toxic when metabolized due to the release of cyanide from the cyanuric chloride linking group.

The production of arginine deiminase via recombinant DNA techniques also provides for certain disadvantages. For example, arginine deiminase produced in Escherichia coli is enzymatically inactive and thus must be denatured and then properly renatured in order for it to become enzymatically active. The usual method for renaturing arginine deiminase produced in *E. coli* is to isolate the inactive enzyme, dissolve it in guanidinium hydrochloride and renature it by rapid dilution into low ionic strength buffer. This last step requires very large volumes of buffer thus making the manufacture of arginine deiminase both expensive and time consuming. However, recombinant technology does have certain advantages. For example, organisms more amenable to fermentation can be used as hosts. Additionally, these fermentation hosts are generally much less pathogenic and larger amounts of arginine deiminase can be obtained. It has been shown the *E. coli* may produce large amounts of Mycoplasma arginine deiminase.

Another problem associated with arginine deiminase is that the enzyme is highly antigenic and thus rapidly cleared from circulation. Accordingly, arginine deiminase must be properly formulated before being used as a therapeutic agent. For purposes of the present invention, the term formulation can be defined as the chemical modification of any arginine deiminase for purposes of reducing antigenicity of the enzyme. For example, it has been shown that the formulation of several proteins including arginine deiminase with polyethylene glycol, i.e. pegylation, can reduce the antigenicity of the protein and greatly increase its circulating half-life. Unfortunately, the formulation of arginine deiminase with polyethylene glycol often inactivates the enzyme.

There is a need for methods and compounds which address these problems associated with the prior art. The present invention is directed to these, as well as other, important ends.

SUMMARY OF THE INVENTION

The present invention relates to a modified arginine deiminase enzyme capable of more efficient production and processing.

The present invention further relates to a recombinant DNA molecule which encodes modified arginine deiminase.

In related aspects, the present invention further relates to recombinant vectors which comprise a nucleotide sequence that encodes modified arginine deiminase and to host cells comprising such vectors.

The present invention further relates to methods for preparing the modified arginine deiminase enzyme of the invention. These methods comprise growing a host cell transformed with the recombinant DNA molecule of this invention in a suitable culture medium.

In other aspects, this invention to methods of treating cancer as well as treating and/or inhibiting the metastasis of tumor cells. The invention also relates to methods of treating parasitic disease, septic shock and other disease states.

These and other aspects of the present invention will be elucidated in the following detailed description of the invention.

BRIEF DESCRIPTION OF THE DRAWINGS

FIG. 1 depicts the amino acid sequence of arginine deiminase cloned from wild-type *Mycoplasma hominus* (SEQ ID NO:1).

FIG. 2 depicts the amino acid sequence of modified arginine deiminase from *Mycoplasma hominus* in accordance with preferred embodiments of the present invention (SEQ ID NO:4).

DETAILED DESCRIPTION OF PREFERRED EMBODIMENTS OF THE INVENTION

The present invention is based on the discovery that modifications of one or more of the naturally occurring amino acid residues of arginine deiminase from *Mycoplasma hominus* can provide for an enzyme that is more easily renatured and formulated thereby improving existing techniques for the manufacture of arginine deiminase and therapeutic compositions comprising the same. The therapeutic compositions of the invention may comprise recombinant DNA molecules, recombinant vectors including plasmids, transformed host cells and other pharmaceutical compositions. The therapeutic compositions may also comprise biocompatible carriers or diluents as known to those skilled in the art. The therapeutic compositions of the invention are easily made sterile and are non-pyrogenic. Such improved techniques and compositions are necessary for the effective treatment of cancer and other disease states.

As used herein, the term "melanoma" may be a malignant or benign tumor arising from the melanocytic system of the skin and other organs, including the oral cavity, esophagus, anal canal, vagina, leptomeninges, and/or the conjunctivae or eye. The term "melanoma" includes, for example, acral-lentiginous melanoma, amelanotic melanoma, benign juvenile melanoma, lentigo maligna melanoma, malignant melanoma, nodular melanoma, subungual melanoma and superficial spreading melanoma.

"Hepatoma" may be a malignant or benign tumor of the liver, including, for example, hepatocellular carcinoma.

"Patient" refers to an animal, preferably a mammal, more preferably a human.

"Biocompatible" refers to materials or compounds which are generally not injurious to biological functions and which will not result in any degree of unacceptable toxicity, including allergenic and disease states.

"Polyethylene glycol" or "PEG" refers to mixtures of condensation polymers of ethylene oxide and water, in a branched or straight chain, represented by the general formula $H(OCH_2CH_2)_nOH$, wherein n is at least 4. It is preferred that the polyethylene glycol is a straight chain. Generally, increasing the molecular weight of the polyethylene glycol decreases the immunogenicity of arginine deiminase. The polyethylene glycol may be used in conjunction with arginine deiminase, and, optionally, a biocompatible linking group, to treat cancer, including, for example, melanomas, hepatomas and sarcomas, preferably melanomas.

Normal cells do not require arginine for growth because they can synthesize arginine from citrulline in a two step process catalyzed by arginosuccinate synthase and arginosuccinate lyase. In contrast, melanomas, hepatomas and some sarcomas do not express arginosuccinate synthase; therefore, they are auxotrophic for arginine, i.e., they require arginine for growth. This metabolic difference may be capitalized upon to develop a safe and effective therapy to treat these forms of cancer. Arginine deiminase catalyzes the conversion of arginine to citrulline, and may be used to eliminate arginine. Thus, arginine deiminase may be utilized as a treatment for melanomas, hepatomas, some sarcomas and other disease states.

The amino acid sequences of arginine deiminase from the *Mycoplasma hominus* gene is disclosed by FIGS. 1 (SEQ ID NO:1) or 2 (SEQ ID NO:4). Chemical and genetic modification of the arginine deiminase enzyme can affect its biological activities. For example, it has been shown that arginine deiminase is typically antigenic and rapidly cleared from circulation in a patient. However, it has also been shown that the formulation of arginine deiminase with polyethylene glycol reduces the antigenicity and increases the circulating half-life of the enzyme. Abuchowski et al., *Cancer Biochem. Biophys.* 7:175–186 (1984); Abuchowski et al., *J. Biol. Chem.* 252:3582–3586 (1977). In particular, arginine deiminase can be covalently modified with polyethylene glycol. Arginine deiminase covalently modified with polyethylene glycol (with or without a linking group) may be hereinafter referred to as "ADI-PEG." In U.S. patent application Ser. No. 09/023,809, Clark describes improved modifications of arginine deiminase from *Mycoplasma hominus* (SEQ ID NO:1), *Mycoplasma arginini* (SEQ ID NO:5), and *Mycoplasma arthritides* (SEQ ID NO:7) with polyethylene glycol, the disclosure of which is hereby incorporated by reference herein in its entirety. When compared to native arginine deiminase, ADI-PEG retains most of its enzymatic activity, is far less antigenic, has a greatly extended circulating half-life, and is much more efficacious in the treatment of tumors. For purposes of the invention, the modification of any arginine deiminase with polyethylene glycol may be referred to as pegylation.

It is necessary, however, to modify arginine deiminase with the maximum amount of polyethylene glycol in order to decrease antigenicity. For example, arginine deiminase can be formulated with the maximum amount of succinimidyl succinate polyethylene glycol (SS-PEG). The SS-PEG attaches to primary amines on proteins (the n-terminus and lysines) during the pegylation process. Unfortunately, it has been shown that the pegylation process can inactivate arginine deiminase if allowed to go to completion. While not meant to limit the present invention in any way, it is presently believed that arginine deiminase is inactivated because polyethylene glycol attaches to sites on the enzyme which interfere with the enzymes ability to catalyze a reaction. Thus, it has traditionally been necessary to carefully determine the exact ratio of SS-PEG to enzyme, concentration of reactant and timeofreaction in order to prevent inactivation while decreasing antigenicity (i.e., optimal pegylation). Additionally, it becomes increasingly difficult to control pegylation reactions as manufacturing scale increases, and often it is necessary to inactivate the SS-PEG prior to removal of excess polyethylene glycol.

It has also been shown that arginine deiminase produced by recombinant technology, in particular arginine deiminase produced in *Escherichia coli* cells, is initially inactive. It has thus been necessary to activate the recombinant arginine deiminase by denaturing and then properly renaturing the enzyme. Typically, the inactive enzyme has been isolated, dissolved in guanidium hydrochloride, and then renatured via rapid dilution with low ionic strength buffer. However, large volumes of buffer are required, thus making the production of recombinant arginine deiminase both expensive and time-consuming.

It has now been discovered that certain modifications of arginine deiminase can facilitate both the renaturation and formulation (i.e., pegylation) of the enzyme thereby improving manufacturing processes. The present invention is based on the unexpected discovery that certain amino acid changes in arginine deiminase provide for excellent results in the recombinant production and formulation of the enzyme. The production of arginine deiminase has traditionally been expensive and time consuming due to difficulties associated with recombinant production and formulation. The present invention thus discloses a modified arginine deiminase that provides for improved renaturation and formulation processes while retaining the ability to convert arginine to citrulline. For purposes of the present invention, modified arginine deiminase can be defined as arginine deiminase having one or more amino acid substitutions. It is to be understood that modified arginine deiminase can include arginine deiminase having a single amino acid substitution or a plurality of amino acid substitutions. The invention also discloses a DNA sequence which encodes for the modified arginine deiminase of the invention. The modified arginine deiminase of the invention can provide for excellent results in the treatment of certain types of cancer, inhibiting the metastasis of cancer, and treating other disease states.

It is to be understood that preferred embodiments of the invention are based on the discovery that certain pegylation sites associated with arginine deiminase may be located at or adjacent the catalytic region of the enzyme. For purposes of the present invention, the phrase "pegylation site" may be defined as any site or position of arginine deiminase that may be covalently modified with polyethylene glycol. A "pegylation site" can be considered located at or adjacent the catalytic region of the enzyme where pegylation of the site results in a significant reduction in catalytic activity of the enzyme. The pegylation of such sites has traditionally resulted in the inactivation of the enzyme. For example, arginine deiminase from *Mycoplasma hominus* has a lysine at the 112 position which is believed to be at or adjacent the catalytic region of the enzyme. The attachment of polyethylene glycol to this lysine at the 112 position may inactivate the enzyme. In addition, arginine deiminase from *Mycoplasma hominus* has a cysteine at the 397 position which is believed to be at or adjacent the catalytic region of the enzyme. The importance of this cysteine has been shown as it has now been discovered that amino acid substitutions for cysteine at the 397 position may inactivate the enzyme. In particular, it has been shown that substituting alanine, histidine, arginine, serine, lysine or tyrosine for cysteine at the 397 position results in a loss of all detectable enzyme activity. Arginine deiminase from Mycoplasma hominus also has three lysines located near this conserved cysteine, in particular $Lys^{374}$, $Lys^{405}$ and $Lys^{408}$. The attachment of polyethylene glycol to $Lys^{374}$, $Lys^{405}$, $Lys^{408}$ or combinations thereof is believed to inactivate the enzyme.

It is to be understood that arginine deiminase derived from other organisms may also have pegylation sites corresponding to 112 position of arginine deiminase from *Mycoplasma hominus*. For example, arginine deiminase from *Steptococcus pyrogenes* has lysine at the 104 position, arginine deiminase from *Mycoplasma pneumoniae* has lysine at the 106 position, and arginine deiminase from Qiardia intestinalis has lysine at the 114 position. In addition, arginine deiminase from some organisms may have lysines corresponding to the same general location as the 112 position of arginine deiminase from *Mycoplasma hominus*. The location of lysine in arginine deiminase from such organisms may be indicated as follows:

TABLE 1

Pegylation sites of arginine deiminase from various organisms

| Organisms producing arginine deiminase | Position of lysine in arginine deiminase |
| --- | --- |
| Mycoplasma hominus (SEQ ID NO:1) | 112 |
| Mycoplasma arginini (SEQ ID NO:5) | 111 |
| Clostridium perfringens | 105 |
| Bacillus licheniformis | 97, 108 |
| Borrelia burgdorferi | 102, 111 |
| Borrelia afzellii | 101 |
| Enterococcus faecalis | 102, 110 |
| Streptococcus pyogenes | 104 |
| Steptococcus pneumoniae | 103 |
| Lactobacillus sake | 97, 106 |
| Qiardia intestinalis | 114, 116 |

It is presently believed that the attachment of polyethylene glycol to such lysines or combinations thereof may inactivate the enzyme. It is presently believed that amino acid substitutions at such lysines may result in a protein that loses less of its enzymatic activity upon pegylation.

The present invention thus provides for certain amino acid substitutions in the polypeptide chain of arginine deiminase. These amino acid substitutions provide for modified arginine deiminase that loses less activity upon pegylation; i.e. upon pegylation, the reduction of enzyme activity following pegylation in the modified arginine deiminases is less than the reduction of enzyme activity following pegylation in the unmodified arginine deiminases. By eliminating pegylation sites at or adjacent to the catalytic region of enzyme, optimal pegylation can be achieved without the traditional loss of activity. As discussed above, arginine deiminase from certain organisms have pegylation sites located at various positions on the peptide chain. While not limiting the present invention, it is presently believed that arginine deiminase may have the amino acid lysine located at or adjacent to the catalytic region of the enzyme and that pegylation of these sites may inactivate the enzyme. By eliminating at least one of these pegylation sites, pegylation can be achieved and more enzyme activity retained. In accordance with the invention, it is preferred that lysine is substituted with glutamic acid, valine, aspartic acid, alanine, isoleucine, leucine or combinations thereof. More preferred is that lysine is substituted with glutamic acid. In one embodiment of the invention, it is preferred that modified arginine deiminase from *Mycoplasma hominus* has an amino acid substitution at $Lys^{112}$, $Lys^{374}$, $Lys^{405}$, $Lys^{408}$ or combinations thereof. Preferably, modified arginine deiminase from *Mycoplasma hominus* has an amino acid substitution $Lys^{112}$ to $Glu^{112}$, $Lys^{374}$ to $Glu^{374}$, $Lys^{405}$ to $Glu^{405}$, $Lys^{408}$ to $Glu^{408}$ or preferred is that modified arginine deiminase from *Mycoplasma hominus* has lysine at position 112 substituted with glutamic acid (SEQ ID NO:2).

It is to be understood that other preferred embodiments of the invention are based on the discovery that certain structural characteristics of arginine deiminase may prevent or interfere with the proper and rapid renaturation of arginine deiminase when produced via recombinant technology. In particular, these structural characteristics hinder or prevent the enzyme from assuming an active conformation during recombinant production. For purposes of the present invention, the phrase "active conformation" may be defined as a three-dimensional structure that allows for enzymatic activity by unmodified or modified arginine deiminase. The active conformation may, in particular, be necessary for catalyzing the conversion of arginine into citrulline. The phrase "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominus* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma hominus*.

The present invention thus again provides for certain amino acid substitutions in the polypeptide chain of arginine deiminase. Such amino acid substitutions can eliminate the problematic structural characteristics in the peptide chain of arginine deiminase. Such amino acid substitutions provide for improved renaturation of the modified arginine deiminase. These amino acid substitutions make possible rapid renaturing of modified arginine deiminase using reduced amounts of buffer. These amino acid substitutions may also provide for increased yields of renatured modified arginine deiminase. In one embodiment of the invention, it is preferred that the modified arginine deiminase have a single amino acid substitution at $Pro^{210}$. As mentioned above, arginine deiminase derived from *Mycoplasma hominus* has the amino acid proline located at the 210 position. While not limiting the present invention, it is presently believed that the presence of the amino acid proline at position 210 results in a bend or kink in the normal polypeptide chain that increases the difficulty of renaturing (i.e., refolding) arginine deiminase. Substitutions for proline at position 210 make possible the rapid renaturation of modified arginine deiminase using reduced amounts of buffer. Substitutions for proline at position 210 may also provide for increased yields of renatured modified arginine deiminase. In a preferred embodiment, the proline at position 210 is substituted with serine (SEQ ID NO:3). It is to be understood that in accordance with this aspect of the invention, other substitutions at position 210 may be made. Examples of preferred substitutions include $Pro^{210}$ to $Thr^{210}$, $Pro^{210}$ to $Arg^{210}$, $Pro^{210}$ to $Asn^{210}$, $Pro^{210}$ to $Gln^{210}$ or $Pro^{210}$ to $Met^{210}$. By eliminating those structural characteristics associated with the amino acid of position 210 of the wild-type arginine deiminase, proper refolding of the enzyme can be achieved.

In another embodiment of the invention, it is preferred that the modified arginine deiminase have multiple amino acid substitutions. The modified arginine deiminase may have at least one amino acid substitution eliminating pegylation sites at or adjacent a catalytic region of the enzyme. The modified arginine deiminase may also have at least one amino acid substitution eliminating those structural characteristics that interfere with the renaturation of the enzyme. The amino acid substitutions may thus provide for a modified arginine deiminase of the invention. The amino acid substitutions may provide for the pegylation of modified arginine deiminase without a loss of enzymatic activity. The amino acid substitutions may provide for a modified arginine deiminase that can be rapidly renatured using reduced amounts of buffer. The amino acid substitutions may also provide for increased yields of renatured modified arginine deiminase. In a preferred embodiment, the modified arginine deiminase derived from *Mycoplasma hominus* includes the proline at position 210 substituted with serine and the lysine at position 112 substituted with glutamic acid (SEQ ID NO:4). As discussed above, however, it is to be understood that the modified arginine deiminase may include other preferred substitutions.

It is preferred that the modified arginine deiminase of the invention is derived from *Mycoplasma hominus*. In accordance with the invention, however, it will be understood by those skilled in the art that modified arginine deiminase may be derived from other organisms. For example, as discussed above, modified arginine deiminase of the invention can be derived from *Steptococcus pyrogenes, Mycoplasma pneumoniae, Qiardia intestinalis, Mycoplasma hominus, Mycoplasma arginini, Clostridium perfringens, Bacillus licheniformis, Borrelia burgdorferi, Borrelia afzellii, Enterococcus faecalis, Streptococcus pyogenes, Steptococcus pneumoniae, Lactobacillus sake, Qiardia intestinalis*. It is to be understood that modified arginine deiminase may have one or more amino acid substitutions, in accordance with the various aspects of the invention.

It is to be understood that in certain embodiments of the present invention, modified arginine deiminase can be formulated with polyethylene glycol. The present invention provides for the attachment of polyethylene glycol to modified arginine deiminase for increasing circulation half-life, without the traditional inactivation of the enzyme. Traditionally, selection of the attachment site of polyethylene glycol on arginine deiminase was determined by the role of each of the sites within the active domain of the protein, as would be known to the skilled artisan. In accordance with the present invention, polyethylene glycol may be attached to a primary amine of the modified arginine deiminase. The present invention provides for the attachment of polyethylene glycol to the primary amines of arginine deiminase without substantial loss of enzymatic activity. For example, modified arginine deiminase from *Mycoplasma hominus* contains lysine amino acids that may be modified with polyethylene glycol. In other words, these lysines are all possible points at which modified arginine deiminase can be attached to polyethylene glycol. It is to be understood, however, that polyethylene glycol may also be attached to other sites on modified arginine deiminase, as would be apparent to those skilled in the art. Increasing the number of polyethylene glycol units on modified arginine deiminase increases the circulating half life of the enzyme without the traditional decrease in specific activity of the enzyme.

The linking group used to covalently attach polyethylene glycol to modified arginine deiminase may be any biocompatible linking group. As discussed above, "biocompatible" indicates that the compound or group is non-toxic and may be utilized in vitro or in vivo without causing injury, sickness, disease or death. Polyethylene glycol can be bonded to the linking group, for example, via an ether bond, an ester bond, a thiol bond or an amide bond. Suitable biocompatible linking groups include, for example, an ester group, an amide group, an imide group, a carbamate group, a carboxyl group, a hydroxyl group, a carbohydrate, a maleimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. Preferably, the biocompatible linking group is an ester group and/or a maleimide group. More preferably, the linking group is SS, SPA, SCM, SSA or NHS; with SS, SPA or NHS being more preferred, and with SS or SPA being most preferred.

Alternatively, polyethylene glycol may be coupled directly to modified arginine deiminase (i.e., without a linking group) through an amino group, a sulfhydral group, a hydroxyl group or a carboxyl group. Polyethylene glycol may be covalently bonded to modified arginine deiminase via a biocompatible linking group, using methods known in the art, as described, for example, by Park et al, *Cancer Res.*, 33:3–14 (1973); and Zaplipsky and Lee, *Polyethylene Glycol Chemistry: Biotechnical and Biomedical Applications*, J. M. Harris, ed., Plenum Press, NY, Chapter 21 (1992), the disclosures of which are hereby incorporated by reference herein in their entirety.

The present invention also relates to recombinant DNA molecules encoding the modified arginine deiminase of the invention. It is preferred that the DNA molecules comprising the recombinant DNA molecules of this invention are derived from any *Mycoplasma hominus* strain using known techniques, e.g., isolating the gene from a gene bank, making complementary or cDNAs from a mRNA template or via the polymerase chain reaction (see, U.S. Pat. No. 4,800,159) or from isolates of clinical specimens. Alternatively, such recombinant DNA molecules may be synthesized by standard DNA synthesis techniques. Various *Mycoplasma hominus* strains are also publicly available from commercial depositories, e.g., from the American Type Culture Collection (ATCC), Manassas, Va. U.S.A.

The DNA molecules of this invention may comprise additional DNA sequences including, for example, a regulatory element, one or more selectable markers, and sequences that code for replication and maintenance functions. The regulatory region typically contains a promoter found upstream from the coding sequence of this invention, which functions in the binding of RNA polymerase and in the initiation of RNA transcription. In other words, the regulatory element or region can be operatively linked to the coding sequence of this invention. It will be appreciated by one of skill in the art that the selection of regulatory regions will depend upon the host cell employed.

The invention also relates to recombinant vectors, particularly recombinant plasmids that comprise sequences encoding the modified arginine deiminase of the invention.

Another aspect of this invention is a host cell transformed with the recombinant DNA molecule of this invention. Such host cell is capable of growth in a suitable culture medium and expressing the coding sequence of the invention. Such host cell can be prepared by methods of this invention, e.g., by transforming a desired host cell with the plasmid of this invention. Such transformation can be accomplished by utilization of conventional transformation techniques. Furthermore, the recombinant DNA molecule of this invention can be integrated into the host cell's genome by conventional techniques, e.g., homologous recombination. Those host cells suitable for use in the present invention include, but are not limited to, mammalian cells, insect cells, yeast and other bacteria cells, e.g., Streptomyces, Bacillus and Salmonella. It is preferred that the host cells of this invention include those belonging to the species *E. coli*. This invention and the product thereof is not limited to any specific host cell. It is preferred that the modified arginine deiminase is produced by the transformed host cell of this invention, but such enzyme can be prepared by conventional peptide synthesis techniques.

The present invention also relates to methods of producing the enzyme encoded by the recombinant DNA molecule of this invention which comprises culturing the transformed host of the invention in an appropriate culture media and the isolation of such enzyme. For purposes of the present invention, the phrase "appropriate culture media" can be defined as that media which facilitates such host in expressing recombinant DNA molecules encoding the modified arginine deiminase of the invention. It will be appreciated by those skilled in the art that the appropriate culture media will depend upon the host cell used. The isolation of the enzyme so produced can be accomplished from a culture lysate of the host, or if appropriate, directly from the host's culture medium, and such isolation is carried out by conventional protein isolation techniques.

In a preferred embodiment, the DNA coding sequence of the modified arginine deiminase of the invention is expressed in a transformed *Mycoplasma hominus* host cell. Preferably the *Mycoplasma hominus* cell is deficient in arginine deiminase and thus requires complementation. In such systems, sequences that encode the modified arginine deiminase are typically located on a vector. Such vectors contain sufficient amount of bacterial DNA to propagate the vector in *E. coli* or some other suitable host. Such vector also contains a sufficient amount of *Mycoplasma hominus* DNA flanking the enzyme coding sequence so as to permit recombination between a *Mycoplasma hominus* host deficient in the arginine deiminase gene and the heterologous modified arginine deiminase gene. It is to be understood by those skilled in the art that it is not essential to use a *Mycoplasma hominus* host deficient in the modified arginine deiminase gene, but that the absence of the gene in the host prior to recombination will facilitate the screening and isolation of recombinant hosts which have incorporated the gene of interest. The recombinant *Mycoplasma hominus* arising from such homologous recombination can then selected by standard techniques as known to those skilled in the art.

The invention also encompasses methods for the treatment of cancer and/or other disease states comprising the administration of a therapeutically effective amount of one of the compounds of the present invention. A therapeutically effective amount of one of the compounds of the present invention is an amount that is effective in reducing the incidence of the disease state. Where the disease state is cancer, a therapeutically effective amount of one of the compounds of the present invention can be an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. PEG-ADI may be mixed with a phosphate buffered saline solution, or any other appropriate solution known to those skilled in the art, prior to injection. The PEG-ADI formulation may be administered as a solid (lyophalate) or as a liquid formulation, as desired.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. As one skilled in the art will recognize, administration of the PEG-ADI composition of the present invention can be carried out, for example, orally, intranasally, intraperitoneally, parenterally, intravenously, intralymphatically, intratumorly, intramuscularly, interstitially, intra-arterially, subcutaneously, intraocularly, intrasynovial, transepithelial, and transdermally.

EXAMPLES

The invention is further demonstrated in the following examples, which are for purposes of illustration, and are not intended to limit the scope of the present invention.

Example 1

Cloning and Site-directed Mutagenisis of ADI

Cultures of Mycoplasma hominus (ATCC 23114) were obtained from the American Type Culture, Manassas, Va. DNA was extracted and the gene coding for arginine deiminase isolated by the polymerase chain reaction.

The arginine deiminase gene was subcloned into pGEM-t and the E. coli strain JM101. Site directed mutagenesis was performed using the Altered Sites II kit (Promega, Madison, Wis.).

Modified arginine deiminase was expressed in JM101 cells as previously described by Takaku et al., supra. The modified arginine deiminase included glutamic acid at the 112 position and serine at the 210 position. The amino acid sequence of modified arginine deiminase from Mycoplasma hominus is described in FIG. 2 (SEQ ID NO:4).

Example 2

Renaturation and Purification of Enzymatically Active ADI

The modified arginine deiminase (SEQ ID NO:4) was isolated and purified as previously described by Takaku et al., supra. However, several improvements were observed.

TABLE 2

Renaturation of Arginine Deiminase

| Compound | Time (° C.) | Dilution Ratio | Yield |
|---|---|---|---|
| Arginine Deiminase (SEQ ID NO:1) | 90 hours (15° C.) | 1:200 | 70 mg/L |
| Modified Arginine Deiminase (SEQ ID NO:4) | 6–12 hours (room temp.) | 1:50 | 500 mg/L |

As indicated by Table 2 above, renaturation of the modified arginine deiminase was completed at room temperature in about 6 to 12 hours using a 1:50 dilution ratio of guanidium hydrochloride inclusion bodies in buffer. In contrast, Takaku et al. reported that renaturation required 90 hours at 15° C. using a 1:200 dilution ratio. In addition, the yield of modified arginine deiminase was routinely about 500 mg per liter of fermentation whereas Takaku et al. reported a yields of approximately 70 mg per liter of fermentation.

Example 3

Formulation of Modified ADI With PEG

Modified arginine deiminase (SEQ ID NO:4) was formulated using SS-PEG as previously described. The pegylation process was allowed to go unchecked for over 4 hours without the modified arginine deiminase becoming inactivated. In addition, it was not necessary to quench the pegylation process through the addition of glycine. With reference to Table 3, approximately 70–80% of enzymatic activity of the modified arginine deiminase was retained.

TABLE 3

Specific Enzyme Activity (IU/mg protein)

|  | Without Pegylation | Pegylated |
|---|---|---|
| wild type ADI (SEQ ID NO:1) | 20–21 | 5–8 |
| modified ADI (SEQ ID NO:4) | 20–21 | 12–16 |

This indicates that the modified arginine deiminase allows for more consistent formulations. In addition, the modified arginine deiminase allows for scaling up of the manufacturing process as compared to the wild-type arginine deiminase.

Each of the patents, patent applications and publications described herein are hereby incorporated by reference in their entirety.

Various modifications of the invention, in addition to those described herein, will be apparent to one skilled in the art in view of the foregoing description. Such modifications are also intended to fall within the scope of the appended claims.

It is to be understood that the specification of the present application hereby incorporates by reference the claims and their disclosures in their entirety.

What is claimed is:

1. An arginine deiminase isolated from Mycoplasma hominis comprising the amino acid sequence of SEQ ID NO: 1, wherein said deiminase has been modified by elimination of at least one pegylation site at or adjacent to the catalytic region of the delminase.

2. The arginine deiminase of claim 1, wherein the arginine deiminase has been modified to be free of at least one lysine at position 112, 374, 405 or 408 of SEQ ID NO:1.

3. The arginine deiminase of claim 2, wherein the arginine deiminase has been modified by substituting at least one lysine at position 112, 374, 405 or 408 of SEQ ID NO:1 with glutamic acid, valine, aspartic acid, alanine, isoleucine, or leucine.

4. The arginine deiminase of claim 3, wherein the arginine deiminase has been modified by substituting the lysine at position 112 of SEQ ID NO:1 with glutamic acid, valine, aspartic acid, alanine, isoleucine, or leucine.

5. The arginine deminiase of claim 1 having an amino acid sequence comprising SEQ ID NO:2.

6. The arginine deiminase of claim 1 that has been further modified by the substitution or deletion of at least one proline.

7. The arginine deiminase of claim 6, wherein the arginine deiminase has been modified by substitution or deletion of the proline at position 210 of SEQ ID NO:1.

8. The arginine deiminase of claim 7, wherein the arginine deiminase has been modified by substitution of the proline at position 210 of SEQ ID NO:1 with serine, threonine, arginine, asparagine, glutamine, or methionine.

9. The arginine deiminase of claim 8, wherein the arginine deiminase has been modified by substitution of the proline at position 210 of SEQ ID NO:1 with Ser.

10. The arginine deiminase of claim 6 having an amino acid sequence comprising SEQ ID NO:4.

11. The arginine deiminase of claim 1 covalently bound to polyethylene glycol.

12. The arginine deiminase of claim 11 wherein the arginine deiminase is covalently bound to the polyethylene glycol via a linking group.

13. A composition comprising the arginine deiminase of any one of claims 1, 2–4, 5–12 and at least one carrier, diluent, or excipient.

* * * * *

SEQUENCE LISTING

<160> NUMBER OF SEQ ID NOS: 10

<210> SEQ ID NO 1
<211> LENGTH: 409
<212> TYPE: PRT
<213> ORGANISM: Mycoplasma hominis

<400> SEQUENCE: 1

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
```

```
                  355                 360                 365
Thr Asn Ala Ala Leu Lys Ala Ala Gly Ile Thr Val Leu Pro Phe His
                370                 375                 380
Gly Asn Gln Leu Ser Leu Gly Met Gly Asn Ala Arg Cys Met Ser Met
385                 390                 395                 400
Pro Leu Ser Arg Lys Asp Val Lys Trp
                405

<210> SEQ ID NO 2
<211> LENGTH: 409
<212> TYPE: PRT
<213> ORGANISM: Mycoplasma hominis

<400> SEQUENCE: 2

Met Ser Val Phe Asp Ser Lys Phe Asn Gly Ile His Val Tyr Ser Glu
1               5                   10                  15
Ile Gly Glu Leu Glu Thr Val Leu Val His Glu Pro Gly Arg Glu Ile
                20                  25                  30
Asp Tyr Ile Thr Pro Ala Arg Leu Asp Glu Leu Leu Phe Ser Ala Ile
            35                  40                  45
Leu Glu Ser His Asp Ala Arg Lys Glu His Gln Ser Phe Val Lys Ile
        50                  55                  60
Met Lys Asp Arg Gly Ile Asn Val Val Glu Leu Thr Asp Leu Val Ala
65                  70                  75                  80
Glu Thr Tyr Asp Leu Ala Ser Lys Ala Ala Lys Glu Glu Phe Ile Glu
                85                  90                  95
Thr Phe Leu Glu Glu Thr Val Pro Val Leu Thr Glu Ala Asn Lys Glu
            100                 105                 110
Ala Val Arg Ala Phe Leu Leu Ser Lys Pro Thr His Glu Met Val Glu
        115                 120                 125
Phe Met Met Ser Gly Ile Thr Lys Tyr Glu Leu Gly Val Glu Ser Glu
130                 135                 140
Asn Glu Leu Ile Val Asp Pro Met Pro Asn Leu Tyr Phe Thr Arg Asp
145                 150                 155                 160
Pro Phe Ala Ser Val Gly Asn Gly Val Thr Ile His Phe Met Arg Tyr
                165                 170                 175
Ile Val Arg Arg Arg Glu Thr Leu Phe Ala Arg Phe Val Phe Arg Asn
            180                 185                 190
His Pro Lys Leu Val Lys Thr Pro Trp Tyr Tyr Asp Pro Ala Met Lys
        195                 200                 205
Met Pro Ile Glu Gly Gly Asp Val Phe Ile Tyr Asn Asn Glu Thr Leu
210                 215                 220
Val Val Gly Val Ser Glu Arg Thr Asp Leu Asp Thr Ile Thr Leu Leu
225                 230                 235                 240
Ala Lys Asn Ile Lys Ala Asn Lys Glu Val Glu Phe Lys Arg Ile Val
                245                 250                 255
Ala Ile Asn Val Pro Lys Trp Thr Asn Leu Met His Leu Asp Thr Trp
            260                 265                 270
Leu Thr Met Leu Asp Lys Asn Lys Phe Leu Tyr Ser Pro Ile Ala Asn
        275                 280                 285
Asp Val Phe Lys Phe Trp Asp Tyr Asp Leu Val Asn Gly Gly Ala Glu
        290                 295                 300
Pro Gln Pro Gln Leu Asn Gly Leu Pro Leu Asp Lys Leu Leu Ala Ser
305                 310                 315                 320
```

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
                355                 360                 365

Thr Asn Ala Ala Leu Lys Ala Ala Gly Ile Thr Val Leu Pro Phe His
                370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 3
<211> LENGTH: 409
<212> TYPE: PRT
<213> ORGANISM: Mycoplasma hominis

<400> SEQUENCE: 3

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Gln Ser Phe Val Lys Ile
            50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
                100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                180                 185                 190

His Pro Lys Leu Val Lys Thr Pro Trp Tyr Tyr Asp Pro Ala Met Lys
            195                 200                 205

Met Ser Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
                260                 265                 270

Leu Thr Met Leu Asp Lys Asn Lys Phe Leu Tyr Ser Pro Ile Ala Asn
            275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
                355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 4
<211> LENGTH: 409
<212> TYPE: PRT
<213> ORGANISM: Mycoplasma hominis

<400> SEQUENCE: 4

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Gln Ser Phe Val Lys Ile
            50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Lys Glu Glu Phe Ile Glu
                85                  90                  95

Thr Phe Leu Glu Glu Thr Val Pro Val Leu Thr Glu Ala Asn Lys Glu
                100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                180                 185                 190

His Pro Lys Leu Val Lys Thr Pro Trp Tyr Tyr Asp Pro Ala Met Lys
            195                 200                 205

Met Ser Ile Glu Gly Gly Asp Val Phe Ile Tyr Asn Asn Glu Thr Leu
            210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val

```
                      245                 250                 255
Ala Ile Asn Val Pro Lys Trp Thr Asn Leu Met His Leu Asp Thr Trp
                260                 265                 270

Leu Thr Met Leu Asp Lys Asn Lys Phe Leu Tyr Ser Pro Ile Ala Asn
            275                 280                 285

Asp Val Phe Lys Phe Trp Asp Tyr Asp Leu Val Asn Gly Gly Ala Glu
        290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Ala Gly Ala
                325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
        370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 5
<211> LENGTH: 409
<212> TYPE: PRT
<213> ORGANISM: Mycoplasma arginini

<400> SEQUENCE: 5

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Lys Leu Val
        115                 120                 125

Glu Ile Met Met Ala Gly Ile Thr Lys Tyr Asp Leu Gly Ile Gly Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205
```

```
Lys Leu Ser Ile Glu Gly Gly Asp Val Phe Ile Tyr Asn Asn Asp Thr
            210             215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 6
<211> LENGTH: 409
<212> TYPE: PRT
<213> ORGANISM: Mycoplasma arginini

<400> SEQUENCE: 6

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Glu Val
            100                 105                 110

Val Val Arg Asn Phe Leu Lys Ala Lys Lys Thr Ser Arg Lys Leu Val
            115                 120                 125

Glu Ile Met Met Ala Gly Ile Thr Lys Tyr Asp Leu Gly Ile Gly Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175
```

-continued

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
            325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
            405

<210> SEQ ID NO 7
<211> LENGTH: 409
<212> TYPE: PRT
<213> ORGANISM: Mycoplasma arthritidis

<400> SEQUENCE: 7

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu Gln Ser Gln Phe Val Ala Ile
            50                  55                  60

Leu Lys Ala Asn Asp Ile Asn Val Val Glu Thr Ile Asp Leu Val Ala
65                  70                  75                  80

Glu Thr Tyr Asp Leu Ala Ser Gln Glu Ala Lys Asp Arg Lys Ile Glu
            85                  90                  95

Glu Phe Leu Glu Asp Ser Glu Pro Val Leu Ser Glu Ala His Lys Lys
            100                 105                 110

Val Val Arg Asn Phe Leu Lys Ala Lys Lys Thr Ser Arg Lys Leu Val
            115                 120                 125

Glu Leu Met Met Ala Gly Ile Thr Lys Tyr Asp Leu Gly Val Glu Ala

```
                130                 135                 140
Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Lys Val Arg Arg Arg Glu Thr Leu Phe Ser Arg Phe Val Phe Arg
            180                 185                 190

Asn His Pro Lys Leu Val Asn Thr Pro Trp Tyr Tyr Asp Pro Ala Met
            195                 200                 205

Lys Leu Ser Ile Glu Gly Gly Asp Val Phe Ile Tyr Asn Asn Asp Thr
        210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asn Lys Phe Leu Tyr Ser Pro Ile Ala
            275                 280                 285

Asn Asp Val Phe Lys Phe Trp Asp Tyr Asp Leu Val Asn Gly Gly Ala
        290                 295                 300

Glu Pro Gln Pro Val Glu Asn Gly Leu Pro Leu Glu Lys Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Ile Ala Ile Arg Pro Gly Val Val Ile Gly Tyr Ser Arg Asn Glu
        355                 360                 365

Lys Thr Asn Ala Ala Leu Lys Ala Ala Gly Ile Lys Val Leu Pro Phe
        370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 8
<211> LENGTH: 409
<212> TYPE: PRT
<213> ORGANISM: Mycoplasma arthritidis

<400> SEQUENCE: 8

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu Gln Ser Gln Phe Val Ala Ile
        50                  55                  60

Leu Lys Ala Asn Asp Ile Asn Val Val Glu Thr Ile Asp Leu Val Ala
65                  70                  75                  80

Glu Thr Tyr Asp Leu Ala Ser Gln Glu Ala Lys Asp Arg Lys Ile Glu
                85                  90                  95
```

-continued

```
Glu Phe Leu Glu Asp Ser Glu Pro Val Leu Ser Glu Ala His Glu Glu
            100                 105                 110

Val Val Arg Asn Phe Leu Lys Ala Lys Lys Thr Ser Arg Lys Leu Val
        115                 120                 125

Glu Leu Met Met Ala Gly Ile Thr Lys Tyr Asp Leu Gly Val Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Lys Val Arg Arg Arg Glu Thr Leu Phe Ser Arg Phe Val Phe Arg
            180                 185                 190

Asn His Pro Lys Leu Val Asn Thr Pro Trp Tyr Tyr Asp Pro Ala Met
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Lys Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Ile Ala Ile Arg Pro Gly Val Val Ile Gly Tyr Ser Arg Asn Glu
        355                 360                 365

Lys Thr Asn Ala Ala Leu Lys Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 9
<211> LENGTH: 409
<212> TYPE: PRT
<213> ORGANISM: Mycoplasma arthritidis

<400> SEQUENCE: 9

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu Gln Ser Gln Phe Val Ala Ile
    50                  55                  60
```

```
Leu Lys Ala Asn Asp Ile Asn Val Val Glu Thr Ile Asp Leu Val Ala
 65                  70                  75                  80

Glu Thr Tyr Asp Leu Ala Ser Gln Glu Ala Lys Asp Arg Lys Ile Glu
             85                  90                  95

Glu Phe Leu Glu Asp Ser Glu Pro Val Leu Ser Glu Ala His Glu Lys
        100                 105                 110

Val Val Arg Asn Phe Leu Lys Ala Lys Lys Thr Ser Arg Lys Leu Val
        115                 120                 125

Glu Leu Met Met Ala Gly Ile Thr Lys Tyr Asp Leu Gly Val Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Lys Val Arg Arg Arg Glu Thr Leu Phe Ser Arg Phe Val Phe Arg
                180                 185                 190

Asn His Pro Lys Leu Val Asn Thr Pro Trp Tyr Tyr Asp Pro Ala Met
                195                 200                 205

Lys Leu Ser Ile Glu Gly Gly Asp Val Phe Ile Tyr Asn Asn Asp Thr
        210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Val Glu Asn Gly Leu Pro Leu Glu Lys Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Ile Ala Ile Arg Pro Gly Val Ile Gly Tyr Ser Arg Asn Glu
                355                 360                 365

Lys Thr Asn Ala Ala Leu Lys Ala Ala Gly Ile Lys Val Leu Pro Phe
        370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 10
<211> LENGTH: 409
<212> TYPE: PRT
<213> ORGANISM: Mycoplasma arthritidis

<400> SEQUENCE: 10

Met Ser Val Phe Asp Ser Lys Phe Lys Gly Ile His Val Tyr Ser Glu
  1               5                  10                  15

Ile Gly Glu Leu Glu Ser Val Leu Val His Glu Pro Gly Arg Glu Ile
```

-continued

```
                    20                  25                  30
Asp Tyr Ile Thr Pro Ala Arg Leu Asp Glu Leu Leu Phe Ser Ala Ile
            35                  40                  45
Leu Glu Ser His Asp Ala Arg Lys Glu Gln Ser Gln Phe Val Ala Ile
 50                  55                  60
Leu Lys Ala Asn Asp Ile Asn Val Val Glu Thr Ile Asp Leu Val Ala
 65                  70                  75                  80
Glu Thr Tyr Asp Leu Ala Ser Gln Glu Ala Lys Asp Arg Lys Ile Glu
            85                  90                  95
Glu Phe Leu Glu Asp Ser Glu Pro Val Leu Ser Glu Ala His Lys Glu
            100                 105                 110
Val Val Arg Asn Phe Leu Lys Ala Lys Thr Ser Arg Lys Leu Val
            115                 120                 125
Glu Leu Met Met Ala Gly Ile Thr Lys Tyr Asp Leu Gly Val Glu Ala
 130                 135                 140
Asp His Glu Leu Ile Val Asp Pro Met Pro Asn Leu Tyr Phe Thr Arg
 145                 150                 155                 160
Asp Pro Phe Ala Ser Val Gly Asn Gly Val Thr Ile His Phe Met Arg
            165                 170                 175
Tyr Lys Val Arg Arg Arg Glu Thr Leu Phe Ser Arg Phe Val Phe Arg
            180                 185                 190
Asn His Pro Lys Leu Val Asn Thr Pro Trp Tyr Tyr Asp Pro Ala Met
            195                 200                 205
Lys Leu Ser Ile Glu Gly Gly Asp Val Phe Ile Tyr Asn Asn Asp Thr
 210                 215                 220
Leu Val Val Gly Val Ser Glu Arg Thr Asp Leu Asp Thr Val Thr Leu
 225                 230                 235                 240
Leu Ala Lys Asn Leu Val Ala Asn Lys Glu Cys Glu Phe Lys Arg Ile
            245                 250                 255
Val Ala Ile Asn Val Pro Lys Trp Thr Asn Leu Met His Leu Asp Thr
            260                 265                 270
Trp Leu Thr Met Leu Asp Lys Asn Lys Phe Leu Tyr Ser Pro Ile Ala
            275                 280                 285
Asn Asp Val Phe Lys Phe Trp Asp Tyr Asp Leu Val Asn Gly Gly Ala
            290                 295                 300
Glu Pro Gln Pro Val Glu Asn Gly Leu Pro Leu Glu Lys Leu Leu Gln
 305                 310                 315                 320
Ser Ile Ile Asn Lys Lys Pro Val Leu Ile Pro Ile Ala Gly Glu Gly
            325                 330                 335
Ala Ser Gln Met Glu Ile Glu Arg Glu Thr His Phe Asp Gly Thr Asn
            340                 345                 350
Tyr Ile Ala Ile Arg Pro Gly Val Val Ile Gly Tyr Ser Arg Asn Glu
            355                 360                 365
Lys Thr Asn Ala Ala Leu Lys Ala Ala Gly Ile Lys Val Leu Pro Phe
 370                 375                 380
His Gly Asn Gln Leu Ser Leu Gly Met Gly Asn Ala Arg Cys Met Ser
 385                 390                 395                 400
Met Pro Leu Ser Arg Lys Asp Val Lys
            405
```